(12) United States Patent
Cowden et al.

(10) Patent No.: US 6,670,339 B1
(45) Date of Patent: Dec. 30, 2003

(54) USE OF SULFATED OLIGOSACCHARIDES IN LOWERING BLOOD TRIGLYCERIDE LEVELS

(75) Inventors: William B. Cowden, Kambah (AU); Christopher R. Parish, Campbell (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/529,455

(22) PCT Filed: Oct. 13, 1998

(86) PCT No.: PCT/AU98/00844

§ 371 (c)(1),
(2), (4) Date: Jun. 9, 2000

(87) PCT Pub. No.: WO99/18974

PCT Pub. Date: Apr. 22, 1999

(30) Foreign Application Priority Data

Oct. 14, 1997 (AU) .............................................. PO 9768

(51) Int. Cl.[7] .......................... A61K 31/737; C07H 3/06
(52) U.S. Cl. .............................. 514/56; 514/61; 514/62; 536/18.7; 536/21; 536/123
(58) Field of Search .......................... 536/18.7, 21, 123; 514/56, 61, 62

(56) References Cited

U.S. PATENT DOCUMENTS

| | | | |
|---|---|---|---|
| 4,496,550 A | 1/1985 | Lindahl et al. | |
| 4,826,827 A | 5/1989 | Lormeau et al. | |
| 4,933,326 A | 6/1990 | Bianchini et al. | |
| 5,739,115 A | * 4/1998 | Fugedi ........................ | 514/14 |
| 5,783,568 A | * 7/1998 | Schlessinger ................. | 514/53 |

FOREIGN PATENT DOCUMENTS

| | | |
|---|---|---|
| AU | A-10397/83 | 7/1983 |
| AU | A-42637/85 | 11/1985 |
| AU | A-12127/92 | 9/1992 |
| AU | A-60524/94 | 10/1994 |
| EP | A2 0208623 | 1/1987 |
| WO | WO 84/01777 | 5/1984 |
| WO | WO 91/15217 | 10/1991 |
| WO | WO 92/18546 | 10/1992 |
| WO | WO 94/29352 | 12/1994 |
| WO | WO 96/09828 | 4/1996 |

OTHER PUBLICATIONS

Angela Horne and Peter Gettins, H NMR Spectroscopic Studies On The Interactions Between Human Plasma Antithrombin III and Defined Low Molecular Weight Heparin Fragments, Biochemistry, Feb. 11, 1992, vol. 34, No. 5, pp. 2286–2294.

Maurice Petitou, Jean–Claude and Jean Choay, European Journal of Biochemistry, Febs, 1998, vol. 176, pp. 637–640.

P.V.G. Menon and P.A. Kurup, Nature Of The Dietary Carbohydrate and Metabolism Of Glycosaminoglycans and Glycoproteins In Rats, Department Of Biochemistry, University of Kerala, Jul. 30, 1975, pp. 555–562.

Susan P. Williams and Edward A. Johnson, Release Of Lipoprotein Lipase And Hepatic Triglyceride Lipase In Rats By Heparin And Other Sulphated Polysaccharides, Thrombosis Research, 1989, vol. 55, pp. 361–368.

K. Saraswathi Devi and P.A. Kurup, Hypolipidaemic Activity Of Phaseolus Mungo (Blackgram) In Rats Fed A High–Fat–High–Cholesterol Diet, Atherosclerosis, 1972, vol. 15, pp. 223–230.

K. Saraswathi Devi and P.A. Kurup, Hypolipidaemic Activity Of The Protein And Polysaccharide Fraction From Phaseolus Mungo (Blackgram) In Rats Fed A High–Fat–High–Cholesterol Diet, Atherosclerosis, 1973, vol. 18, pp. 389–397.

B. Oswald, F. Shelburne, B. Landis, A. Linker, and S. Quarfordt, The Relevance of A Glycosaminoglycan Sulfates To APO E Induced Lipid Uptake By Hepatocyte Monolayers, Biochemical And Biophysical Research Communications, Nov. 26, 1980, vol. 141, No. 1, 1986, pp. 158–164.

Leidig, G. et al "Effects of heparing and cardiac catheterization on serum lipoprotein and triglyceride level" Am. J. Cardiol., vol 74, pp. 47–52, 1994.*

Monreal, M. et al "Effects of long–term therapy with either heparin or low–molecular weight heparin on serum lipid levels" Haemostasis, vol 25, pp. 283–287, 1995.*

\* cited by examiner

*Primary Examiner*—James O. Wilson
*Assistant Examiner*—Leigh C. Maier
(74) *Attorney, Agent, or Firm*—Fulwider Patton Lee & Utecht, LLP

(57) ABSTRACT

The present invention relates generally to sulfated oligosaccharides, and in particular to the use of certain sulfated oligosaccharides as agents for lowering blood levels of triglycerides such as, for example in treatment of hypertriglyceridaemia.

7 Claims, 3 Drawing Sheets

USE OF SULFATED OLIGOSACCHARIDES IN LOWERING BLOOD TRIGLYCERIDE LEVELS

RELATED APPLICATIONS

This application claims priority from PCT International Application No. PCT/AU98/00844, having the international filing date of Oct. 13, 1998, and Australian Application No. PO 9768, filed Oct. 14, 1997.

FIELD OF THE INVENTION

The present invention relates generally to sulfated oligosaccharides, and in particular to the use of certain sulfated oligosaccharides as agents for lowering blood levels of triglycerides such as, for example in treatment of hypertriglyceridaemia.

BACKGROUND TO THE INVENTION

It has been proposed that triglycerides may be an independent risk factor for coronary artery disease[1-3] and a major study has shown that elevated triglyceride levels, with elevated total cholesterol/HDL cholesterol in coronary patients are associated with an increased risk of further coronary events[4]. Various forms of hypertriglyceridaernia are associated with varying morbidity[5] and one study has shown that plasma triglyceride concentrations have a high predictive power for coronary arterial disease in women[6-7].

A number of studies have shown that treatment with heparin, a high molecular weight, N,O-sulfated polysaccharide, affects blood triglyceride levels[8,9]. Other studies have shown that a heparin derivative, Fragmin, also affects blood triglyceride levels[9]. Results from various studies with heparin have been inconsistent with regard to effects on triglycerides. Thus, for example, Schrader et al. found that treatment with unfractionated heparin caused a significant increase in triglyceride levels but Fragmin caused no change in triglyceride levels[10]. Leidig et al. found that acute treatment with heparin invariably caused a decrease in blood levels of triglycerides[8]. Monreal et al., on the other hand, found that chronic treatment with either heparin or Fragmin caused substantial but not statistically significant increases in blood levels of triglycerides[9].

These variable results are probably due to the immense structural diversity of the glycosaminoglycan heparin. It would be anticipated that sulfated oligosaccharides, which are structurally more homogeneous, would more reproducibly and predictably affect blood triglyceride levels.

A number of agents are used to treat hypertriglyceridaemia and its complications including, inter alia, the fibrates, HMG CoA reductase inhibitors and bile acid-binding resins[11], although none of these are ideal.

Prior International Patent Application No. PCT/AU96/00238 discloses the preparation of a class of sulfated oligosaccharides based on polymers of monosaccharide units linked by 1→2, 1→3, 1→4 and/or 1→6 glycosidic bonds and consisting of from 3 to 8 monosaccharide units, which are potent inhibitors of mammalian heparanases, and can be used to inhibit human angiogenesis, tumour metastasis and inflammation.

In work leading to the present invention, it has been shown that these sulfated oligosaccharides may also be used to lower blood levels of triglycerides.

SUMMARY OF THE INVENTION

In accordance with one aspect, the present invention provides a method of lowering blood triglyceride levels in a human or other warm blooded animal which method comprises administering to said animal an effective amount of a sulfated oligosaccharide of Formula (I):

$$R_1-(R_x)_n-R_2 \quad (I)$$

wherein each of $R_1$, $R_2$ and $R_x$ is a monosaccharide unit which may be the same or different and wherein the monosaccharide units are linked by 1→2, 1→3, 1→4 and/or 1→6 glycosidic bonds; and n is an integer from 1 to 6.

Preferably, the sulfated oligosaccharides has Formula (II):

$$Rx-(Rx)_n-Rx \quad (II)$$

wherein Rx represents the same monosaccharide unit with adjacent monosaccharide units being linked by 1→2, 1→3, 1→4 and/or 1→6 glycosidic bonds, and n is an integer of from 1 to 5 and preferably 3 or 4.

As used herein, terms such as "lowering of blood levels of triglycerides" or "lowering of circulating triglyceride levels" are intended to encompass both prophylactic and therapeutic treatment of a patient in need of such treatment.

DETAILED DESCRIPTION OF THE INVENTION

Figure 1:
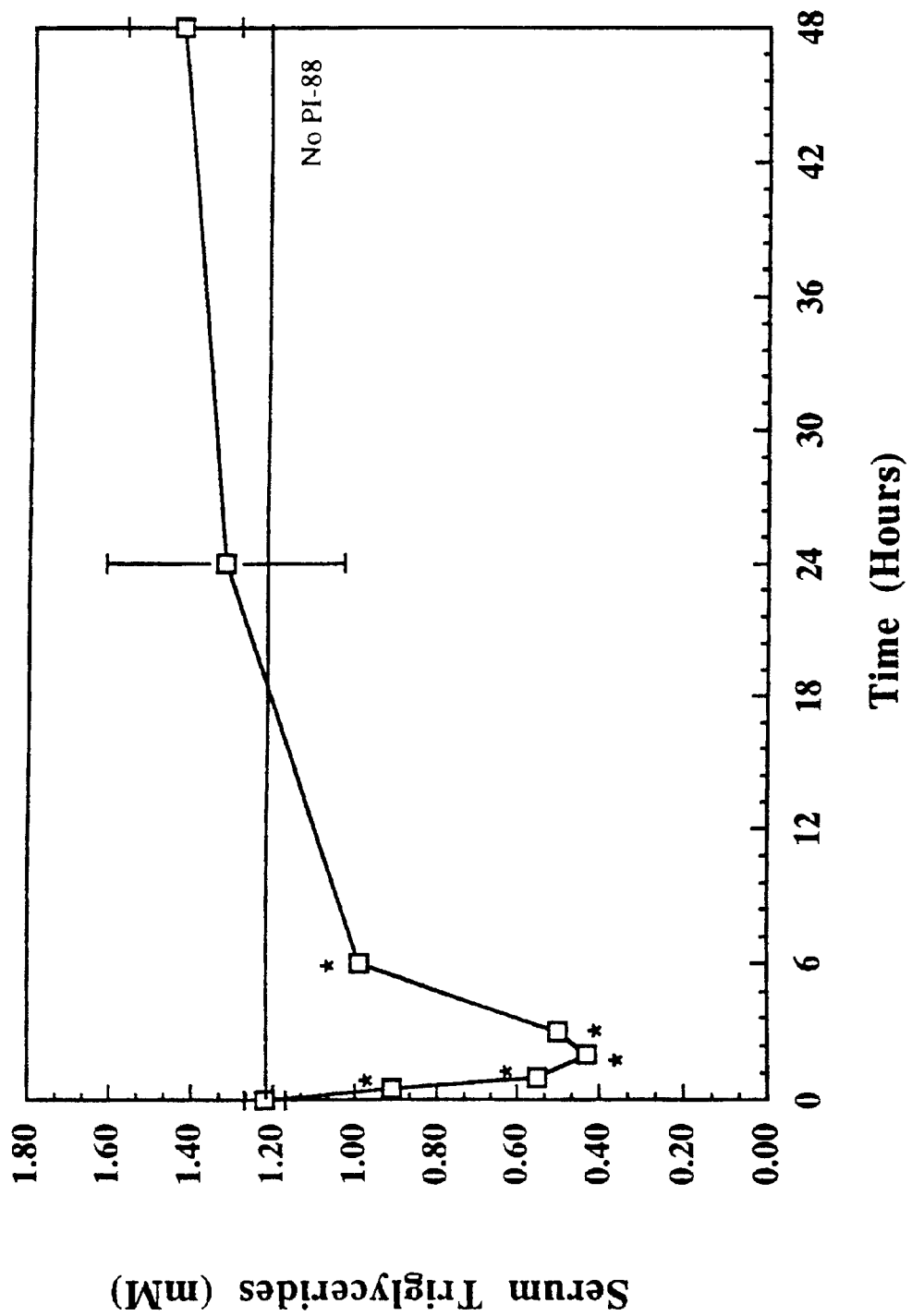
FIG. 1. Time course of the effect of a single s.c. dose (50 mg/kg) of sulfated mannopentaose phosphate (PI-88) on serum triglyceride levels, as measured by the Sigma triglyceride assay. Data presented as group means±SEM (n=4). Time points when a significant reduction in serum triglyceride levels was detected are marked with an asterisk.

The sulfated oligosaccharides which are used in accordance with this invention are based on polymers of monosaccharide units, which may be linked by 1→2, 1→3, 1→4 and/or 1→6 glycosidic bonds and which may consist of from 3 to 8 monosaccharide units. Preferably, the oligosaccharides consist of from 3 to 6 monosaccharide units (that is n of Formulae I and II is from 4 to 4), more preferably from 5 to 6 monosaccharide units (n of Formulae I and II is from 3 to 4). The polymers may comprise homopolymers containing only one type of monosaccharide unit, or heteropolymers containing two or more different types of monosaccharide units, although homopolymers are preferred.

The monosaccharide units which are linked together to form the oligosaccharides are preferably hexoses, and may be either furanoses such as fructose or pyranoses such as glucose, mannose, altrose, allose, talose, galactose, idose, or gulose. Particularly preferred hexoses are glucose and mannose. The hexoses may be in either the D- or the L-configuration.

Each monosaccharide unit may be a hexose, hexuronic, hexosamine or N-acetylhexosamine.

The oligosaccharides of general Formulae I and II also include compounds wherein the monosaccharide units are derivatised, in particular where the units are phosphate, acetyl or other ester derivatives of monosaccharides.

In general, the sulfated oligosaccharides of this invention may be prepared by sulfation of oligosaccharides by methods known per se in the art to give their corresponding O-sulfated derivatives. Suitable sulfation methods are described in International Patent Application No. PCT/AU96/00238, the contents of which are incorporated by reference. The oligosaccharides to be sulfated may be naturally occurring products including oligosaccharides occurring naturally as such (for example raffinose and stachyose), as well as oligosaccharides prepared by enzymatic or chemical degradation of naturally occurring polysaccharides (such as amylose, dextran, cellulose, laminarin, pectin, chitin, chitosan, mannan, and a phosphomannan exopolysaccharide from the yeast *Pichia holstii*). Alternatively, the oligosaccharides may be prepared synthetically by the process disclosed in International Patent Application No. PCT/AU96/00238.

Preferably, the method of the present invention is applied to subjects, humans or other warm blooded animals, in need of treatment. The term "need" means both in response to a disease condition or in the maintenance of a particular level of health to prevent the development of a disease condition.

Reference to "lowering" triglyceride levels may be conveniently measured relative to a reference standard or relative to the subject being treated over time. The term "lowering" includes reducing, decreasing or preventing formation of triglycerides.

In yet another aspect, the present invention extends to the use of at least one sulfated oligosaccharide as described above in lowering blood triglyceride levels in a human or other warm-blooded animal. In particular, the present invention provides for the use of a sulfated oligosaccharide of Formula (I):

$$R_1-(R_x)_n-R_2 \qquad (I)$$

wherein each of $R_1$, $R_2$ and $R_x$ is a monosaccharide unit which may be the same or different and the monosacharide units are linked by 1→2, 1→3, 1→4 and/or 1→6 glycosidic bonds; and n is an integer from 1 to 6; in the manufacture of a medicament for the prphylaxis or treatment of a human or warm blooded animals to lower blood triglyceride levels.

Furthermore, this invention also provides a composition such as a pharmaceutical or veterinary composition for lowering blood triglyceride levels in a human or other warm-blooded animal patient in need of such treatment, which comprises at least one sulfated oligosaccharide as described above, together with one or more pharmaceutically or veterinarily acceptable carriers or diluents therefor.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

The formulation of therapeutic compositions is well known to persons skilled in this field. Suitable pharmaceutically or veterinarily acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically and veterinarily active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active component, use thereof in the pharmaceutical and veterinary compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human or animal subjects to be treated; each unit containing a predetermined quantity of active component calculated to produce the desired therapeutic effect in association with the required pharmaceutical or veterinary carrier and/or diluent. The specifications for the novel dosage unit forms of the invention are dictated by and directly dependent on (a) the unique characteristics of the active component and the particular therapeutic effect to be achieved, and (b) the limitations inherent in the art of compounding such an active component for the particular treatment.

A variety of administration routes are available, although oral delivery is preferred because of the convenience to the patient. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, transdermal or parenteral (e.g. subcutaneous, intramuscular and intravenous) routes. Other routes include intrathecal administration directly into spinal fluid, direct introduction such as by various catheter and balloon angioplasty devices well known to those of ordinary skill in the art, and intraparenchymal injection into targeted areas.

Compositions of the present invention suitable for oral administration may be presented as discrete units such as capsules, cachets, tablets or lozenges, each containing a predetermined amount of the active component, in liposomes or as a solution or suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

As previously described, in accordance with this invention the sulfated oligosaccharides may be used for lowering blood triglyceride levels, particularly in the treatment of hypertriglyceridaemia and its complications.

Throughout this specification, unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

Preparation of Sulfated Oligosaccharides

Two sources of oligosaccharides may be used for subsequent sulfation. The first source represents oligosaccharides derived from naturally occurring polysaccharides. The usual preparation procedure involves partial depolymerisation of the polysaccharide by enzymatic or chemical means and size fractionation of the resultant oligosaccharides. Examples of polysaccharides from which oligosaccharides may be generated are amylose, dextran, cellulose, laminaran, pectin, chitin, chitosan, mannan and a phosphomannan exopolysaccharide from the yeast *Pichia holstii*. The second source represents totally synthetic hexose-containing oligosaccharides prepared by chemical polymerisation of hexose monomers. Prior International Patent Application No. PCT/AU96/00238 discloses a method for the manufacture of these totally synthetic oligosaccharides. This International patent application also describes a procedure for the isolation of a mannopentaose phosphate of the structure P-6-Man-α-(1→3)-Man-α-(1→3)-Man-α-(1→3)-Man-α-(1→2)Man from the exopolysaccharide of the yeast *Pichia holstii*. Other naturally occurring oligosaccharides may be purchased commercially, for example from Seikagaku, Tokyo, Japan. Finally, all of the oligosaccharides may be sulfated by a procedure disclosed in International Patent Application No. PCT/AU96/00238, the contents of which are incorporated herein by reference.

EXAMPLE 2

This Example shows the use of daily doses of sulfated oligosaccharides to lower blood levels of triglycerides. A mannopentaose phosphate from the exopolysaccharide of the yeast *Pichia holstii* was isolated and sulfated by the procedure disclosed in International Patent Application No. PCT/AU96/00238, and used in the following experiments.

1. Nine 10 week old female Fisher rats were treated with the sulfated mannopentaose phosphate or saline over a 7 day period as follows. On day 10 the rats were weighed and placed into three groups of three rats based on weight. On every subsequent morning their weights were recorded. Each morning beginning on day 1 at approximately 8.00 AM and evening at approximately 8.00 PM the rats were injected in the following manner. The control group received sterile normal saline solution 100 $\mu$l s.c. One treatment group received the sulfated mannopentaose phosphate at a dose of 10 mg/kg s.c. in an injection volume of 100 $\mu$l of sterile saline solution. Thus, each rat in this group received a total daily dose of 20 mg/kg. Animals in the second treatment group received the sulfated mannopentaose phosphate at a dose of 50 mg/kg s.c. in an injection volume of 100 $\mu$l of sterile saline solution. Thus, each rat in this group received a total daily dose of 100 mg/kg. This injection routine was repeated for a total of 7 days.

On the morning of day 8 of the experiment, the rats were anaesthetised and blood was taken for triglyceride analysis. Triglyceride levels were determined using a commercially available assay kit (Sigma, Triglyceride—GPO-Trinder). Each animal in the two treatment groups showed a substantial drop in blood levels of triglycerides when compared to the animals in the control group. Thus, blood triglyceride levels in the control group averaged 1.43±0.13 mmol/L, in the 20 mg/kg/day treatment group blood triglyceride levels averaged 0.3±0.12 mmol/L and in the 100 mg/kg/day treatment group blood triglyceride levels averaged 0.1±0.0 mmol/L.

2. In a second experiment the sulfated mannopentaose phosphate was found to reduce blood triglyceride levels in both male and female Lewis rats. Thus, on day 0 the rats were weighed and placed into three groups of the same sex, containing three rats each based on weight. On every subsequent morning their weights were recorded. Each morning beginning on day 1 at approximately 8.00 AM and each evening at approximately 8.00 PM the rats were injected in the following manner. The control groups received sterile normal saline solution 100 $\mu$l s.c. The first treatment groups of male and female rats received the sulfated mannopentaose phosphate, at a dose of 10 mg/kg s.c. in 100 $\mu$l of sterile saline solution (total daily dose 20 mg/kg). The second treatment groups of male and female rats received the sulfated mannopentaose phosphate at a dose of 50 mg/kg s.c. (total daily dose 100 mg/kg). This injection routine was repeated for a total of 7 days.

On morning of day 8 of the experiment, the rats were anaesthetised and blood was taken for triglyceride analysis. Triglyceride levels were determined using a commercially available assay kit (Sigma, Triglyceride—GPO-Tinder).

Each animal in the four treatment groups showed a substantial drop in blood levels of triglycerides when compared to the animals in the appropriate control group. Thus, blood triglyceride levels in the male control group averaged 1.7±0.21 mmol/L, in the mg/kg/day male treatment group averaged 0.9±0.2 mmol/L and in the 100 mg/kg/day male treatment group averaged 0.3±0.0 mmol/L. Blood triglyceride levels in the female control group averaged 1.13±0.19 mmol/L, and in the 20 mg/kg/day female treatment group averaged 0.5±0.0 mmol/L and in the 100 mg/kg/day female treatment group averaged 0.17±0.03 mmol/L.

EXAMPLE 3

This Example shows that a single treatment with the sulfated mannopentaose phosphate of Example 1 causes a decrease in blood levels of triglycerides in a dose-responsive manner. Thus, 20 CBA/h female mice 8–10 weeks old were weighed and placed into five groups, containing four mice each based on weight. The control group was injected with sterile normal saline solution 100 µl s.c. The respective treatment groups were injected with sulfated mannopentaose phosphate at doses of 10, 20, 50 or 100 mg/kg s.c. in a volume of 100 µl of sterile normal saline solution. Two hours following injection, mice were anaesthetised and blood was collected via cardiac puncture and allowed to clot and serum triglyceride levels were measured using a commercially available kit (Sigma, Triglyceride—GPO-Trinder). Each dose of sulfated mannopentaose phosphate caused a reduction in blood triglyceride levels, with a significant reduction being observed with doses of 10 mg /kg and above (FIG. 1).

EXAMPLE 4

This Example shows that an alternate daily treatment with a single injection of the sulfated mannopentaose phosphate of Example 1 causes a sustained decrease in blood levels of triglycerides. Thus, 10 CBA/h female mice 8–10 weeks old were weighed and divided into two groups of 5 mice each based on weight. Mice in the control group were injected with sterile normal saline solution 100 µl s.c. on alternate days for a total of 4 injections. Mice in the treatment group were injected with the sulfated mannopentaose phosphate at a dose of 50 mg/kg s.c. on alternate days for a total of 4 injections. Twenty-four hours following the last injection, blood (50 µl) was collected from the tail veins of each animal and assayed for triglyceride levels (Sigma, Triglyceride—GPO-Trinder). Blood triglyceride levels in the control group averaged 1.11±0.1 mM and blood triglyceride levels in the treatment group averaged 0.64±0.04 mM.

EXAMPLE 5

This Example shows that continuous infusion of the sulfated mannopentaose phosphate of Example 1 is effective at reducing blood levels of triglycerides. Thus, 10 CBA/h female mice 8–10 weeks old were weighed and divided into two groups of 5 mice each based on weight. Mice in the control group were implanted subcutaneously with a mini-osmotic pump (Alzet 2001) containing sterile normal saline solution. Mice in the treatment group were implanted subcutaneously with a mini-osmotic pump containing the sulfated mannopentaose phosphate which delivered the sulfated mannopentaose phosphate at a dose of 50 mg/kg/day. At the end of the 7 day period over which the mini-osmotic pumps delivered their payload, blood (50 µl) was collected from the tail veins of mice from both groups and assayed for triglycerides (Sigma, Triglyceride—GPO-Trinder). Triglyceride levels in the blood from mice in the control group averaged 1.49±0.23 mM and triglyceride levels in the blood of mice in the treatment group averaged 1.01±0.07 mM. One week following the treatment period, blood triglyceride levels were measured again in each group and levels in the treatment group had returned to normal, or those approximating the control group. Thus, at this point levels of triglycerides in the blood of mice in the control group averaged 1.29±0.08 mM and levels of triglycerides in the blood of mice in the treatment group averaged 1.27±0.06 mM.

EXAMPLE 6

Figure 2:
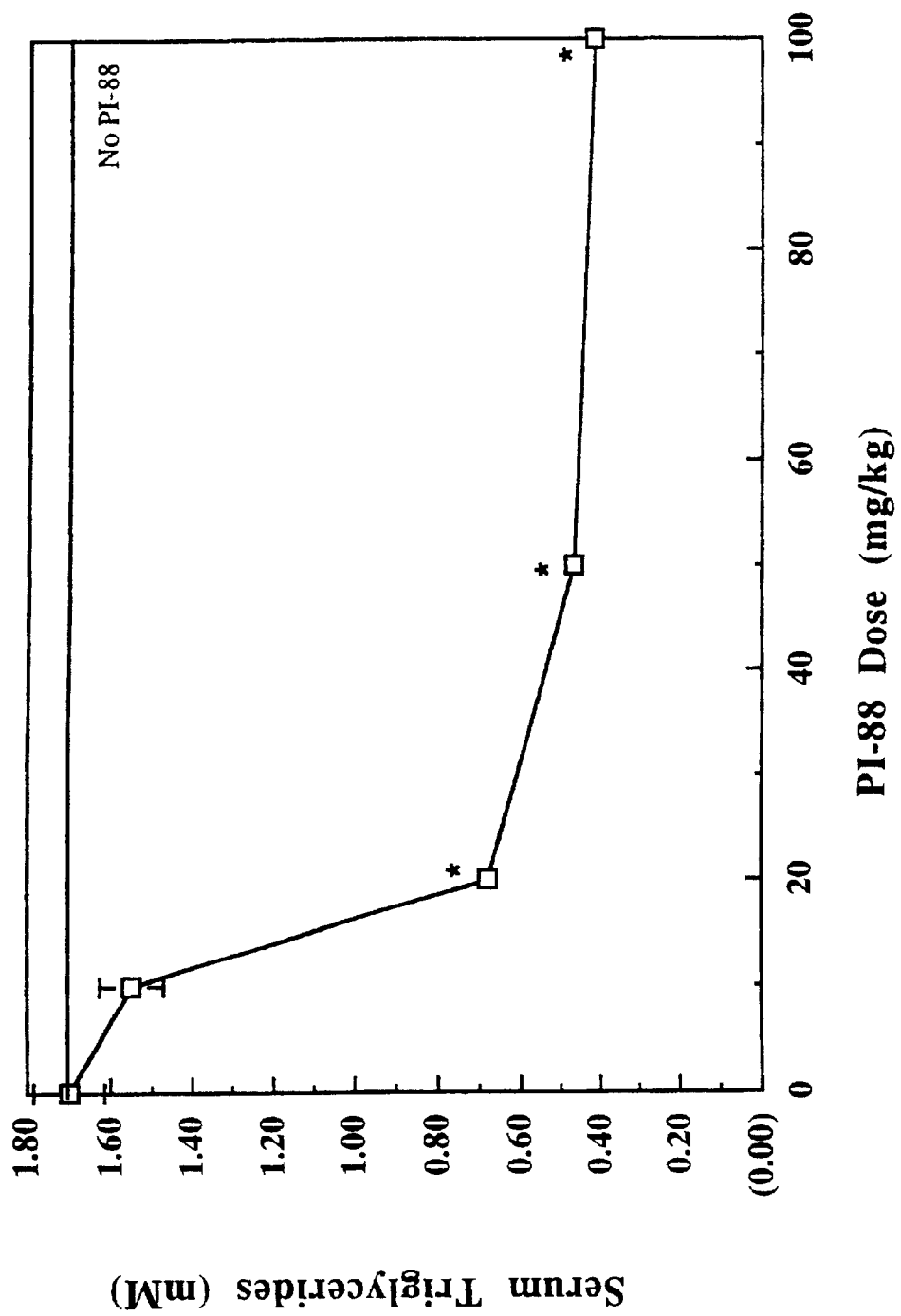
FIG. 2. Effect of different single doses of sulfated mannopentaose phosphate (PI-88) (10–100 mg/kg) on serum triglyceride levels 2 hours following s.c. injection. Data presented as group means±SEM (n=4). Doses of PI-88 which resulted in a significant reduction in serum triglyceride levels are marked with an asterisk.

This Example shows that a single treatment with sulfated mannopentaose phosphate of Example 1 causes a decrease in blood triglyceride levels in a time dependent manner. Thus, 32 CBA/h female mice 8–10 weeks old were weighed and placed into eight groups, containing four mice each based on weight. The control group was injected with sterile normal saline solution 100 µl s.c. All the treatment groups were injected with sulfated mannopentaose at a dose of 50 mg/kg s.c. in a volume of 100 µl of sterile normal saline solution. At 0.5, 1, 2, 3, 6, 24 and 48 hours following injection mice were anaesthetised and blood was collected via cardiac puncture and allowed to clot and serum triglyceride levels were measured using a commercially available kit (Sigma, Triglyceride—GPO-Trinder). A significant reduction in blood triglyceride levels was observed within 0.5 hours of sulfated mannopentaose phosphate injection and triglyceride levels continued to fall until 2 hours following injection of the compound (FIG. 2). After 3 hours triglyceride levels slowly returned to normal although they were still significantly lower than controls 6 hours after sulfated mannopentaose phosphate injection, returning to normal by the 24 hour time point (FIG. 2).

EXAMPLE 7

Figure 3:
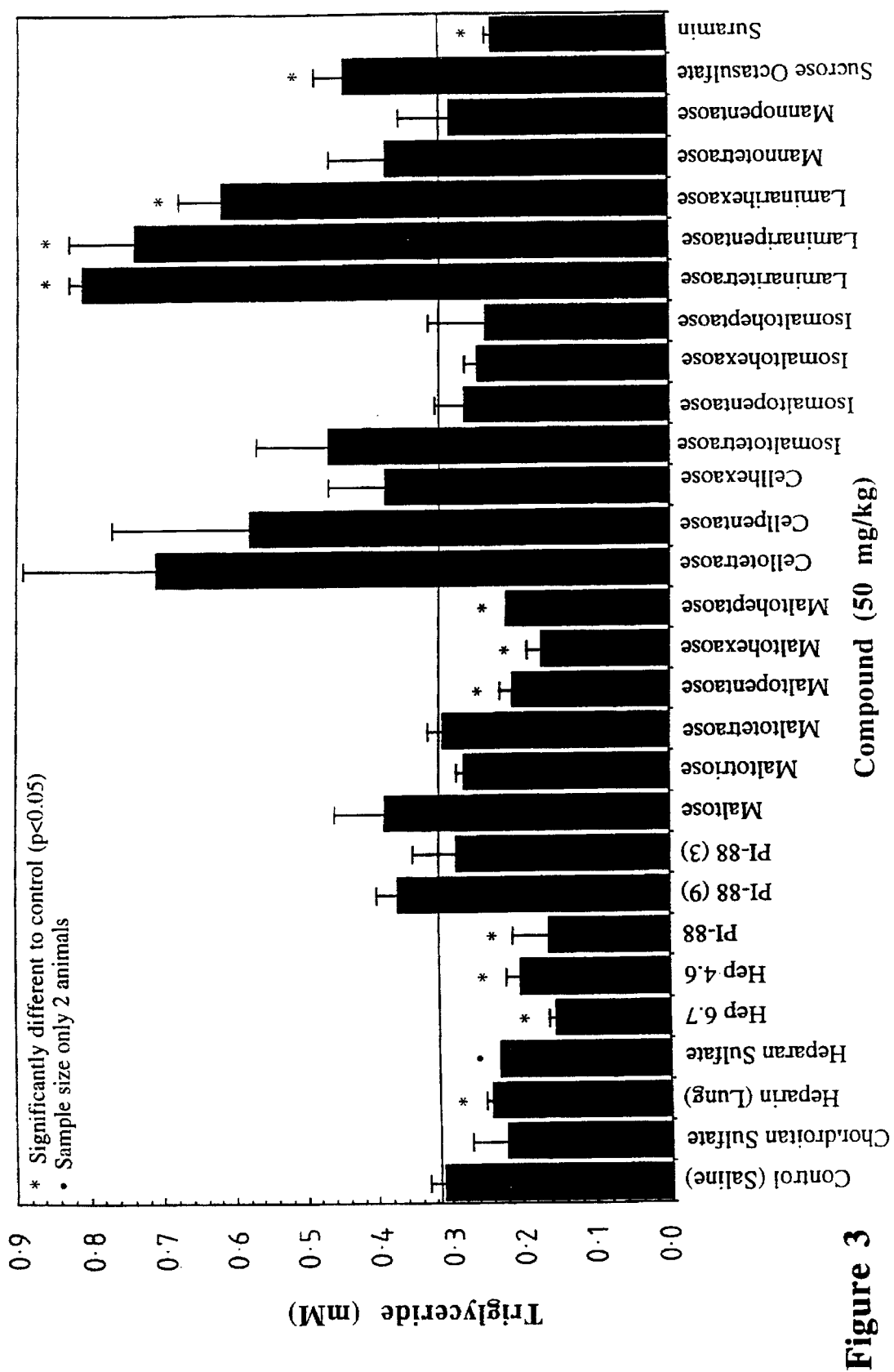
FIG. 3. Ability of different glycosaminoglycans and sulfated oligosaccharides to lower serum triglyceride levels in CBA mice. Compounds were injected s.c. at a dose of 50 mg/kg, blood samples taken 2 hours later and assayed for triglyceride content. Each histogram is the mean±SEM (n=3) for each treatment.

This Example shows that sulfated oligosaccharides other than sulfated mannopentaose phosphate can lower blood triglyceride levels. Mice (CBA/h female mice 8–10 weeks old) were injected s.c. with a range of glycosaminoglycans and sulfated oligosaccharides at a dose of 50 mg/kg and 2 hours later mice were anaesthetised, blood was collected via cardiac puncture and allowed to clot and serum triglyceride levels measured using a commercially available kit (Sigma, Triglyceride—GPO-Trinder). Triglyceride levels were measured at this time point as Example 6 shows that sulfated mannopentaose phosphate induces maximum lowering of serum triglycerides 2 hours following administration. Of the 28 compounds tested only 8 were shown to significantly lower serum triglyceride levels 2 hours after the injection of a dose of 50 mg/kg (FIG. 3). Three of the triglyceride lowering compounds were heparin derivatives, either heparin itself or two low molecular weight heparin preparations (FIG. 3). As shown in Examples 2–6, sulfated mannopentaose phosphate (termed PI-88 in FIG. 3) also lowered serum triglyceride levels, with only fully sulfated PI-88 being active, ie., PI-88 preparations containing 3 and 9 sulfate groups/molecule were ineffectual compared with the fully sulfated mannopentaose phosphate which contains approx sulfite groups/molecule. Of the remaining four compounds which significantly lowered triglyceride levels, three were maltose containing oligosaccharides, namely maltopentaose, maltohexaose and maltoheptaose sulfate. The only other compound with some activity was suramin, a sulfonated compound which has previously been used as an angiogenesis and heparanase inhibitor. An interesting aspect of this study was that several of the sulfated oligosaccharides tested actually enhanced serum triglyceride levels, particularly the cellobiose and laminarin derived oligosaccharides, with sucrose octasulfate also showing a small but significant enhancement (FIG. 3). These data suggest that the sulfated oligosaccharides, which are structurally relatively homogeneous, are mimicing structural features of heparin that either reduce or enhance blood triglyceride levels.

EXAMPLE 8

This Example shows that the ability of sulfated oligosaccharides to lower blood triglyceride levels correlates with their ability to interfere with the lipoprotein lipase—heparan sulfate interaction. It has been noted previously[8-10] that heparin lowers blood triglyceride levels due to its ability to displace heparan sulfate-bound lipoprotein lipase from blood vessel endothelium. The released enzyme then cleaves fatty acids from plasma triglycerides and thereby lowers blood triglyceride levels.

As a more rapid and direct means of measuring the ability of different sulfated oligosaccharides to release lipoprotein lipase from the endothelium, an in vitro assay for this effect was developed. The assay involved immobilising lipoprotein lipase (10 $\mu$g/ml in PBS, 15 hr, 4° C.), purified from bovine milk as previously described[12], in 96 well plastic microplates (50 $\mu$l/well). Non-specific binding sites were then blocked by the addition of 200 $\mu$l/well of PBS containing 1% (w/v) bovine serum albumin (BSA) for 2 hr at 4° C. Following three washes with 200 $\mu$l/well of PBS/0.05% Tween 20 (PBST), 50 $\mu$l/well of either biotinylated bovine lung heparin or biotinylated porcine mucosal heparan sulfate (Sigma), used at either 1 or 10 $\mu$g/ml, was added and incubated for 2 hr at 4° C. Following three washes with PBST, 50 $\mu$l/well of europeum-streptavidin (1 ng/ml in PBS/1% BSA) was added for 1 hr at 4° C., the plate again washed three times with PBST, enhancement solution (50 $\mu$l/well) added and bound europeum measured by time resolved fluorescence detection using a Delfia Research Fluorometer (Wallac, Turku, Finland). Inhibition assays measured the ability of different sulfated oligosacchandes to inhibit the binding of biotinylated heparan/heparin sulfate to the immobilised lipoprotein lipase enzyme.

Using this assay, a wide range of sulfated compounds were tested and the results of these studies are summa in Table 1. As expected, heparin is a potent inhibitor of the binding of lipoprotein lipase to heparin and heparan sulfate. However, in all three assays depicted in Table 1, fully sulfated mannopentaose phosphate (PI-88) was at least as good as, and in one case better than, heparin at inhibiting lipoprotein lipase binding. Of particular interest was the observation that the degree of sulfation of PI-88 was of critical importance. It was found that only the most highly sulfated PI-88 was inhibitory (15 sulfates/molecule), whereas the less sulfated PI-88s (9 and 3 sulfates/molecule) totally lacked inhibitory activity. This result agrees with the in vivo triglyceride lowering activity of PI-88 depicted in FIG. 3 and discussed in Example 7. Furthermore, many of the other sulfated oligosaccharides tested also totally lacked inhibitory activity. For example, with the maltose series, only maltohexaose and maltoheptaose were inhibitory, with the laminarin and isomaltose series none of the oligosaccharides were inhibitory, and with the cellobiose series only cellohexaose exhibited activity. Other compounds that lacked activity were sucrose octasulfate, suramin and three sulfated maltose dimers which were provided by Luitpold Ltd and which have previously been shown to have modest heparanase inhibitory activity. On the other hand, totally synthetic mannotetraose and mannopentaose sulfates prepared as disclosed in prior International Patent Application No. PCT/AU96/00238 exhibited modest to high activity. It also appears that with heparin itself, chain length is critical, as the lower molecular weight heparins are much less active, particularly when higher concentrations of biotinylated heparin are used in the assay. Collectively, these data suggest that highly sulfated PI-88 and maltohexaose sulfate are potent inhibitors of lipoprotein lipase binding, with most of the other sulfated oligosaccharides exhibiting negligible inhibitory activity. These data are generally consistent with the in vivo activity of the sulfated oligosaccharides shown in Example 7.

Persons skilled in this art will appreciate that variations and modifications may be made to the invention as broadly described herein, other than those specifically described without departing from the spirit and scope of the invention. It is to be understood that this invention extends to include all such variations and modifications.

TABLE 1

Ability of Different Sulfated Oligosaccharides to Inhibit the Binding of Heparin/Heparan Sulfate to Lipoprotein Lipase[a]

| Inhibitor | IC50 ($\mu$g/ml)[b] | | |
|---|---|---|---|
| | Biotinylated Heparin (10 $\mu$g/ml) | Biotinylated Heparin (1 $\mu$g/ml) | Biotinylated Heparan Sulfate (10 $\mu$g/ml) |
| Heparin (lung) | 5 | 0.5 | 0.1 |
| Chondroitin SO$_4$ | — | >200 | >200 |
| Heparin SO$_4$ (mucosal) | — | >200 | — |
| Heparin 6.7 kDa (mucosal) | >100 | 5 | — |
| Heparin 4.6 kDa (mucosal) | >100 | 9 | — |
| Heparin 3.1 kDa (mucosal) | >100 | >100 | — |
| PI-88 (15 SO$_4$/molecule) | 3 | 1 | 0.1 |
| PI-88 (9 SO$_4$/molecule) | — | >100 | >100 |
| PI-88 (3 SO$_4$/molecule) | — | >100 | >100 |
| Maltose, maltotriose, -tetraose & -pentaose SO$_4$ | >100 | >100 | — |
| Maltohexaose SO$_4$ | 6 | 3 | — |
| Maltoheptaose SO$_4$ | 12 | 3 | — |
| Cellotetraose & -pentaose SO$_4$ | >100 | — | — |
| Cellohexaose | 12 | — | — |
| Isomaltotetraose, -pentaose, -hexaose and -heptaose SO$_4$ | >100 | — | — |
| Laminaritetraose, -pentaose and -hexaose SO$_4$ | >100 | — | — |
| Mannotetraose SO$_4$ (synthetic) | — | 28 | — |
| Mannopentaose SO$_4$ (synthetic) | — | 9 | 0.1 |
| Luitpold maltose dimer SO$_{4s}$ (10078, 10121, 10086)[c] | >100 | >100 | — |
| Sucrose octasulfate | — | >200 | — |
| Suramin | >100 | >100 | — |

[a]Assay involves immobilizing bovine milk lipoprotein lipase on plastic and inhibiting the binding of either biotinylated bovine lung heparin (1 $\mu$g/ml or 10 $\mu$g/ml) or biotinylated porcine mucosal heparan sulfate (10 $\mu$g/ml) to the enzyme with different sulfated compounds. Bound heparin/heparan sulfate is then assessed by europeum-streptavidin binding and time resolved fluorescence detection.
[b]IC50 = concentration of inhibitor which inhibits binding of biotinylated heparin/heparan sulfate by 50%.
[c]Maltose dimer sulfates linked by different hydrocarbon spacers and supplied by Luitpold Ltd.

REFERENCES:

1. Barbir, M., Wile, D., Trayner, I., Aber, V. R., and Thompson, G. R., *Br. Heart J.*, 60:397–403, 1988.
2. Kukita, H. Imamura, Y., Hamada, M., Tadafumi, J., and Kokubu, T. *Atherosclerosis*, 42:21–29, 1982.
3. Reardon, M. F., Nestel, P. J., Craig, I. H., and Harper, R. W. *Circulation*, 71:881–888, 1985.
4. Manninen, V., Tenkanen, L., Koskinen, O., Huttunen, J. K., Manttari, M., Heinonen, O. P., and Frick, M. H. *Circulation*, 85:37–45, 1992.
5. Eckel, R. H. *New England J. Med.*, 320:1060–1068, 1989.
6. Castelli, W. P. *Am. Heart J.*, 106:1191–1200, 1983.
7. Castelli, W. P. *Am. J. Obstet. Gynecol.*, 158:1553–1560, 1988.
8. Leidig, G. A. Jr., Pastemak, R. C., Horowitz, G., and Ginsburg, G. S. *Am. J. Cardiol.*, 74:47–52, 1994.
9. Monreal, M., Lafoz, E., Urritia, A., Roncales, J., Galimany, R., Biosca, C., and Corominas, A. *Haemostasis*, 25:283–289, 1995.
10. Schrader, J., Stibbe, W., Armstrong, V. W., Kandt, M., Muche, R., Kostering, H., Seidel, D., and Scheler, F. *Kidney Int.*, 33:890–896, 1988.
11. Witztum, J. L. Drugs used in the treatment of hyperlipoproteinemias. *In: The Pharmacological Basis of Therapeutics*, 9th Edition. pp 875–897. G. Hardman, L. E. Limburd, P. B., Molinoff, R. W. Ruddon, A. G. Gilman, Eds. McGraw-Hill, New York, 1996.
12. Socorro, L., Green, C. C., and Jackson, R. L. *Prep. Biochem.*, 15:133–143, 1985.

What is claimed is:

1. A method of lowering blood triglyceride levels in a human or other warm blooded mammal in need of such treatment, which method comprises administering to said mammal an effective amount of a fully sulfated oligosaccharide of Formula (I):

$$R\text{—}(R)_n\text{—}R \tag{I}$$

wherein each R is a pyranose unit and wherein the pyranose units are linked by $\alpha 1 \rightarrow 2$, $1 \rightarrow 3$, $1 \rightarrow 4$ and/or $1 \rightarrow 6$ glycosidic bonds; and n is an integer having a value of 3, 4 or 5.

2. The method according to claim 1 wherein pyranose is selected from the group consisting of glucose, mannose, altrose, allose, talose, galactose, idose and gulose.

3. The method according to claim 2 wherein pyranose is glucose or mannose.

4. The method according to claim 1, wherein said oligosaccharide is phoshomannopentaose.

5. The method according to claim 4, wherein said phosphomannopentaose is isolated from *Pichia holstii*.

6. The method according to claim 1, wherein said oligosaccharide is selected from the group consisting of maltopentaose, maltohexaose and maltoheptaose.

7. The method according to claim 1, wherein said oligosaccharide is administered as a composition comprising at least one pharmaceutically acceptable carrier and/or diluent.

* * * * *